US006534259B1

(12) United States Patent
Wakefield

(10) Patent No.: US 6,534,259 B1
(45) Date of Patent: Mar. 18, 2003

(54) REGRESSIVE BEHAVIORAL DISORDER DIAGNOSIS

(76) Inventor: Andrew Wakefield, 43 Taylor Avenue, Kew Gardens, Surrey (GB), TW94EB ( * ) Notice: Subject to any disclaimer, the term of this patent is extended or adjusted under 35 U.S.C. 154(b) by 0 days.

(21) Appl. No.: 09/445,388

(22) PCT Filed: Jun. 4, 1998

(86) PCT No.: PCT/GB98/01637

§ 371 (c)(1), (2), (4) Date: Mar. 23, 2000

(87) PCT Pub. No.: WO98/55138

PCT Pub. Date: Dec. 10, 1998

(30) Foreign Application Priority Data

Jun. 6, 1997 (GB) .............................................. 9711663

(51) Int. Cl.[7] .................................................. C12Q 1/70
(52) U.S. Cl. .......................................................... 435/5
(58) Field of Search ........................... 435/5; 424/212.1, 424/219.1, 534, 520, 529

(56) References Cited

U.S. PATENT DOCUMENTS 5,466,714 A * 11/1995 Isaacs et al. ................. 514/558
5,874,226 A * 2/1999 Zeytinoglu et al. ........... 435/71

FOREIGN PATENT DOCUMENTS

| | | | |
|---|---|---|---|
| EP | 0101200 | * 2/1988 | ........... C07G/17/00 |
| WO | 0 010 738 A | 5/1980 | |
| WO | 0 101 200 A | 2/1984 | |
| WO | WO 96 30544 A | 10/1996 | |

OTHER PUBLICATIONS

Peltola et al. The Lancet 351:1327–1328, May 2, 1998.*
Taylor et al. The lancet 353:2026–2029, Jun. 12, 1999.*
Azfal et al. Bulletin of the World Health Organization 78(2): 199–204, 2000.*
Washington Post, Apr. 24, 2001.*
Chadwick et al. Journal of MEdical Virology 55:305–311, 1998.*
Luzi et al, The Lancet 350:338–339, Aug. 2, 1997.*
Hunsinger et al. Life Sciences 67:1667–1682, 2000.*

* cited by examiner

*Primary Examiner*—Mary E. Mosher
(74) *Attorney, Agent, or Firm*—Licata & Tyrrell P.C.

(57) ABSTRACT

The invention provides a method for the diagnosis of regressive behavioral disease (RBD) from a body derived sample, which method comprises performing an assay for persistent measles infection in said sample. The invention also concerns a pharmaceutical composition for the treatment of an MMR virus mediated disease comprising a transfer factor (TF) formed by the dialysis of virus-specific lymphocytes to a molecular weight filter cut-off of 12,500 disposed in a pharmaceutically acceptable carrier or diluent therefore.

3 Claims, 4 Drawing Sheets

| MCS* | 8411<br>TGCTTCCAGC (SEQ ID NO:1) | 8441<br>CAAGCACTCT (SEQ ID NO:2) | 8471<br>CCATTGAAGG (SEQ ID NO:3) |
|---|---|---|---|
| VACCINE (SCHWARZ) | --------A- | ---------- | ---------- |
| SPORADIC WILD STRAIN | | | |
| EDMONSTON (1960') | ---------- | ---------- | ---------- |
| - 1985 | ---------- | ---------- | ---------- |
| 1985-89 | ---------- | ---------- | ---------- |
| 1990- | ---------- | ---------- | ---C------ |
| CROHN DISEASE | ---------- | ---------- | ---------- |
| UC | --------A- | ---------- | ---------- |
| AUTISTIC CHILD | ---------- | ---------- | ---------- |
| AUTISTIC CHILD | ---------- | ------A--- | ---------- |
| AUTISTIC CHILD | --------A- | ---------- | ---------- |
| SSPE 81 (UK) | ---------- | ---------- | ---------- |
| SSPE 83 (UK) | ---------- | ---------- | ---------- |
| SSPE 214 (UK) | ---------- | ---------- | ---------- |
| SSPE 300 (UK) | ---------- | ---------- | ---------- |
| SSPE 75 (JAPAN) | ---------- | ---------- | ---------- |
| SSPE 92 (JAPAN) | ---------- | ---------- | ---------- |

| MCS* | 8481<br>ATAACAGGAT (SEQ ID NO:3) | 8491<br>TCCTTCATAC (SEQ ID NO:7) | 8511<br>CTGTTGATCT (SEQ ID NO:8) |
|---|---|---|---|
| VACCINE (SCHWARZ) | ---------- | ---------- | ---------- |
| SPORADIC WILD STRAIN | | | |
| EDMONSTON (1960') | ---------- | ---------- | ---------- |
| - 1985 | ---------- | ------G--- | ---------- |
| 1985-89 | ---------- | ---------- | -----A---- |
| 1990- | -C-------- | ---------- | -----A---- |
| CROHN DISEASE | ---------- | ---------- | ---------- |
| UC | ---------- | ---------- | ---------- |
| AUTISTIC CHILD | ---------- | ---G------ | ---------- |
| AUTISTIC CHILD | -A-------- | -----T---- | ---------- |
| AUTISTIC CHILD | ---------- | ---------- | ---CC----- |
| SSPE 81 (UK) | ---------- | ---------- | ---------- |
| SSPE 83 (UK) | ---------- | ---------- | ---------- |
| SSPE 214 (UK) | ---------- | ---G------ | ---------- |
| SSPE 300 (UK) | -A-------- | ---------- | ---------- |
| SSPE 75 (JAPAN) | ---------- | ---------- | ---------- |
| SSPE 92 (JAPAN) | ---------- | ------G--- | ---------- |

FIG. 1A

| MCS* | 8521<br>GAGTCTGACA (SEQ ID NO:8) | 8531<br>GTTGAGCTTA (SEQ ID NO:8) | 8541<br>AAATCAAAAT (SEQ ID NO:8) |
|---|---|---|---|
| VACCINE (SCHWARZ) | ---------- | ---------- | ---------- |
| SPORADIC WILD STRAIN | | | |
| EDMONSTON (1960') | ---------- | ---------- | ---------- |
| - 1985 | ---------- | ---------- | -------G-- |
| 1985-89 | ---------- | ---------- | ---------- |
| 1990- | ---------- | --------C- | ---------- |
| CROHN DISEASE | ---------- | ---------- | ---------- |
| UC | ---------- | ---------- | ---------- |
| AUTISTIC CHILD | ---------- | ---------- | ---------- |
| AUTISTIC CHILD | ---------- | ---------- | ---------- |
| AUTISTIC CHILD | ---------C | ---------- | ---------- |
| SSPE 81 (UK) | ---------- | ---------- | ---------- |
| SSPE 83 (UK) | ---------- | ---------- | ---------- |
| SSPE 214 (UK) | ---------- | ---------- | ----T----- |
| SSPE 300 (UK) | ---------G | ---------- | ---------- |
| SSPE 75 (JAPAN) | ---------- | ---------- | ---------- |
| SSPE 92 (JAPAN) | ---------- | ---------- | -------G-- |

| MCS* | 8551<br>TGCTTCGGGA (SEQ ID NO:8) | 8581<br>CGGTTCAGGG (SEQ ID NO:10) | 8601<br>ACAAATCCAA (SEQ ID NO:11) |
|---|---|---|---|
| VACCINE (SCHWARZ) | ---------- | ---------- | ---------- |
| SPORADIC WILD STRAIN | | | |
| EDMONSTON (1960') | ---------- | ---------- | ---------- |
| - 1985 | ---------- | ---------- | ---------- |
| 1985-89 | ------A--- | ---------- | -----A---- |
| 1990- | ------A--- | ---------- | ---------- |
| CROHN DISEASE | ---------- | ---------- | ---------- |
| UC | ---------- | ---------- | ---------- |
| AUTISTIC CHILD | ---------- | ---------- | ---------- |
| AUTISTIC CHILD | ---------- | ---------T | ---------- |
| AUTISTIC CHILD | ---------- | ---------- | ---------- |
| SSPE 81 (UK) | ---------- | ---------- | ---------- |
| SSPE 83 (UK) | ---------- | ---------- | ---------- |
| SSPE 214 (UK) | ---------- | ---------- | ---------- |
| SSPE 300 (UK) | ---------- | ---------T | ---------- |
| SSPE 75 (JAPAN) | ---------- | ---------- | ---------- |
| SSPE 92 (JAPAN) | ---------- | ---------- | ---------- |

FIG. 1B

| MCS* | 8621<br>GTGTATTGGC (SEQ ID NO:4) | 8641<br>GCCAATGAAG (SEQ ID NO:5) | 8661<br>TAGGTGTAAT (SEQ ID NO:6) |
|---|---|---|---|
| VACCINE (SCHWARZ) | ---------- | ---------- | ---------- |
| SPORADIC WILD STRAIN | | | |
| EDMONSTON (1960') | ---------- | A--------- | ---------- |
| - 1985 | ---------- | ---------- | ---------- |
| 1985-89 | ---------- | ---------- | ---------- |
| 1990- | ---------- | ---------- | ---------- |
| CROHN DISEASE | ---------- | ---------- | ---------- |
| UC | ---------- | ---------- | ---------- |
| AUTISTIC CHILD | -----C---- | --------G- | ---------- |
| AUTISTIC CHILD | ---------- | ---------- | ---------- |
| AUTISTIC CHILD | ---------- | ---------- | ---------- |
| SSPE 81 (UK) | ---------- | ---------- | ---------- |
| SSPE 83 (UK) | ---------- | ---------- | ---------- |
| SSPE 214 (UK) | ---------- | ---------- | ---------- |
| SSPE 300 (UK) | ---------- | ---------- | ---------- |
| SSPE 75 (JAPAN) | ---------- | ---------- | ---------- |
| SSPE 92 (JAPAN) | -C-------- | ---------- | -G-------- |

FIG. 1C

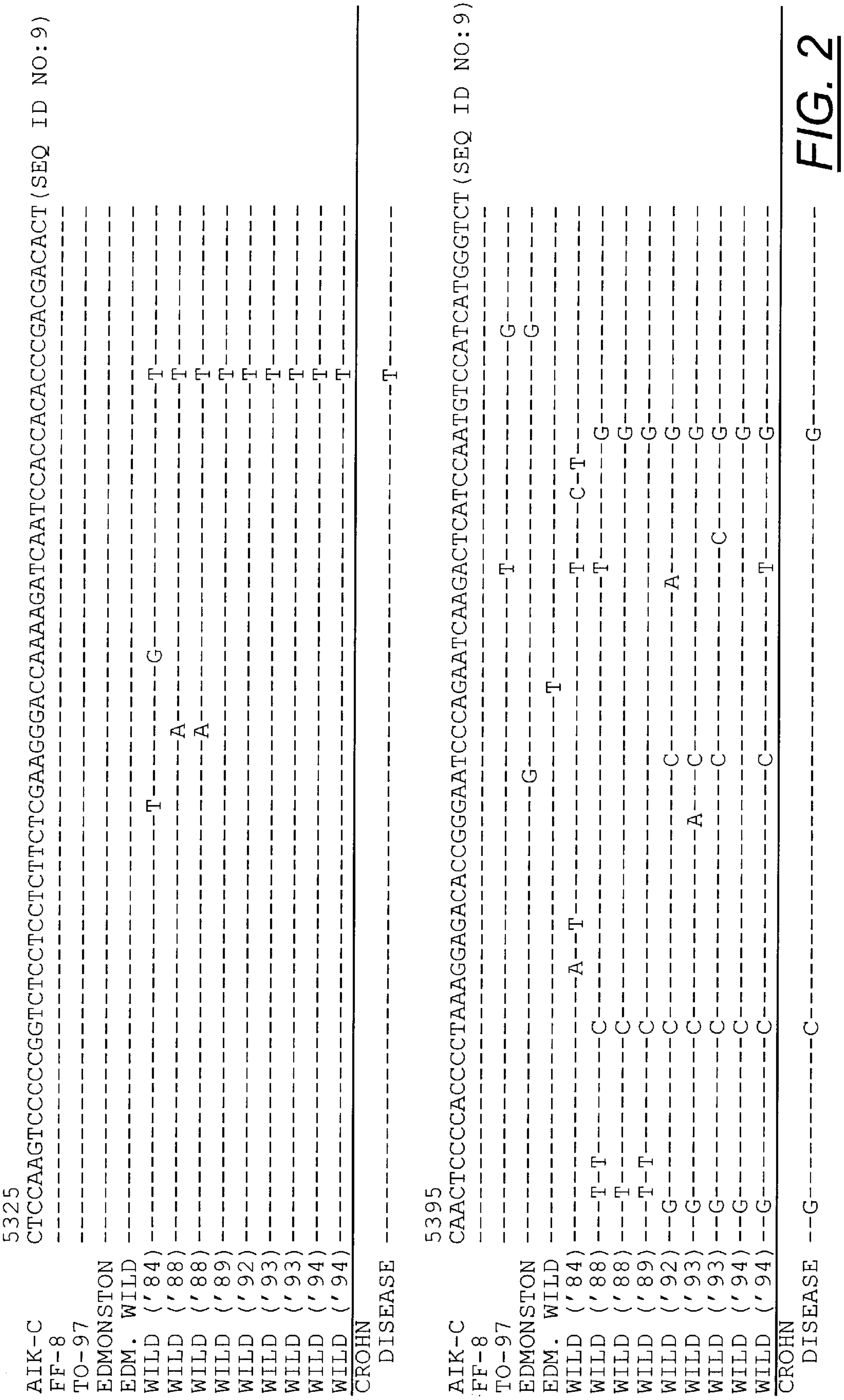

FIG. 2

```
         5325
AIK-C    CTCCAAGTCCCCCGGTCTCCTCCTTCTCGAAGGGACCAAAAGATCAATCCACCACACCCGACGACACT (SEQ ID NO:9)
FF-8     ------------------------------------------------------------------
TO-97    ------------------------------------------------------------------
EDMONSTON ------------------------------------------------------------------
EDM. WILD ------------------------------------------------------------------
WILD ('84) ---------------------------T---------G----------------------------
WILD ('88) ----------------------------------A-------------------------T-----
WILD ('88) ----------------------------------A-------------------------T-----
WILD ('89) ------------------------------------------------------------T-----
WILD ('92) ------------------------------------------------------------T-----
WILD ('93) ------------------------------------------------------------T-----
WILD ('93) ------------------------------------------------------------T-----
WILD ('94) ------------------------------------------------------------T-----
WILD ('94) ------------------------------------------------------------T-----
CROHN
DISEASE  ------------------------------------------------------------T-----

         5395
AIK-C    CAACTCCCCCACCCCTAAAGGAGAGACACCGGGAATCCCAGAATCAAGACTCATCCAATGTCCATCATGGGTCT (SEQ ID NO:9)
FF-8     ------------------------------------------------------------------------
TO-97    ------------------------------------------------------------------------
EDMONSTON ------------------------------------------------------------------------
EDM. WILD ------------------------------------------------------------------------
WILD ('84) -----------A--T---------------------------T-----------------------------
WILD ('88) ---T-T---------------C------------G-----------T-------------T---G------
WILD ('88) ---T-T---------------C------------------------T-------------T---G------
WILD ('89) ---T-T---------------C----------------T----------------C-T-------------
WILD ('92) ----G----------------C---------------------------A--------T------G-----
WILD ('93) ----G----------------C--------------A-C-------T--------------------G----
WILD ('93) ----G----------------C----------------C-------T--------------------G----
WILD ('94) ----G----------------C----------------C--------------C-----------------G
WILD ('94) ----G----------------C----------------C-------T--------------------G----
CROHN
DISEASE  ----G----------------C----------------C-----------------------------G----
```

REGRESSIVE BEHAVIORAL DISORDER DIAGNOSIS

The present invention relates to a new vaccine/immunisation for the prevention and/or prophylaxis against measles virus infection and to a pharmaceutical or therapeutic composition for the treatment of IBD(Inflammatory Bowel Disease); particularly Crohn's Disease and Ulcerative Colitis and regressive behavioural disease (RBD)(also referred to as "Regressive Developmental Disorder").

In my earlier Patent Application No. WO 96/30544 I have described how persistent measles virus infection whether of a wild type or vaccine mediated is the origin of some forms of IBD.

The latest and most comprehensive population-based epidemiological studies put the prevalence of IBD in the United Kingdom population alone at 1 in 185 at the age of 26 rising to 1 in 140 at the age of 31. Since prevalence of these diseases increases with age to give a peak onset in the 30 to 35 year age group, this level is due to reach 1 in 80 by the age of 45. This rise is particularly conspicuous in children where the instance of Crohn's Disease has risen by a factor of up to 6 in some areas since 1968.

At present vaccination is used for the prophylactic prevention of measles virus infection and as a public health measure has proved to be generally effective. Infants are injected with an attenuated virus often within the second year of life and lately a booster vaccination schedule has been introduced to all school children approaching primary school age.

Unfortunately as I have shown previously in the above mentioned patent application the use of this vaccine has been shown to be instrumental in development of Crohn's Disease and other forms of IBD over the ensuing 30 to 40 years and particularly has been instrumental in a substantial increase in Crohn's Disease in children since vaccination was started in 1968.

It has now also been shown that use of the MMR vaccine (which is taken to include live attenuated measles vaccine virus, measles virus, mumps vaccine virus and rubella vaccine virus, and wild strains of the aforementioned viruses) results in ileal lymphoid nodular hyperplasia, chronic colitis and regressive developmental disorder including autism (RBD), in some infants. Before vaccination infants were shown to have a normal developmental pattern but often within days to weeks of receiving the vaccination some infants can begin to noticeably regress over time leading to a clinical diagnosis of autism. The MMR vaccine was first used in 1968 and a study in Sweden has shown recently that the prevalence of children with autism has significantly risen. The study has shown that the autistic spectrum of disorders may now affect 1% of the population.

The Physician is therefore confronted with a difficulty at the individual level in that whereas as a public health measure measles vaccination is called for, it can have unwanted effects in those subjects who are unable to immunologically eliminate the virus so introduced.

This is particularly so when there is at present no cure for IBD; sufferers can expect relapses of their disease requiring potent immunosuppressant therapy or removal of the affected bowel and may be condemned to the use of a ostomomy bag. Nor is there a cure for autism; sufferers have to live in a silent world of their own unable to communicate with the rest of the world.

What is needed therefore is a safer vaccine which does not give rise to these problems, and a treatment for those with existing IBD. I have now discovered a combined vaccine/therapeutic agent which is not only most probably safer to administer to children and others by way of vaccination/immunisation, but which also can be used to treat IBD and RBD whether as a complete cure or to alleviate symptoms.

As disclosed in my earlier patent application Crohn's Disease is most probably caused by a failure of the body to completely eliminate the measles virus, probably because of the failure of the initial dosage of virus to illicit a full immune response, which in turn allows the remaining virus to collect at various sites in the body particularly in the small intestine and colon thereby causing the granulomatous vasculitis associated with Crohn's disease.

Although the mechanism of virus infection is not fully elucidated, it seems likely at present that the mechanism which gives rise to gut granuloma is as follows:

Following an incomplete immune response to an attenuated virus challenge in early life, or indeed less often a wild type infection, measles virus collects in the wall of the gut and particularly in the capillaries supplying blood thereto. At some point, often when a patient is between 20 to 30 years old, this induces a vasculitis which in turn causes necrosis of the overlying epithelium of the gut. I have previously shown that measles virus is present in these granulomatous lesions. It appears that for some reason lymphocytes which bind to the measles virus site fail to eliminate the virus so identified. What is needed therefore is a system for "switching on" the destruct mechanisms of the bound lymphocytes which appear to be disenabled by the persistent measles virus particles.

The compositions of the present invention have the ability not only to condition the recipient to raise a specific immune response to MMR and measles virus when used as a vaccine/immunisation, but also to reestablish the appropriate antiviral immune response of an immune system to persistent measles virus infection in IBD.

I have also found that regressive behavioural disorder (RBD) in children is associated with measles, mumps and rubella (MMR) vaccination. Although it is yet to be established which element, if only one of MMR, for example measles virus, is directly implicated, histological and serological examination of a sample of children who exhibited RBD showed lesions in the gut indicative of the problems which arise in IBD and Crohn's Disease. Further I have reviewed a cohort of children who following a period of apparent normality have lost acquired skills including those of communication. These children all have gastrointestinal symptoms including abdominal pain, diarrhoea, and in some cases food intolerance. It is significant that this syndrome only appeared with the introduction of the polyvalent MMR vaccine in 1988 rather than with the monovalent measles vaccine introduced in 1968. This indicates that MMR is responsible for this condition rather than just the measles virus and that accordingly a transfer factor (vide infra) specific for the components other than the measles virus in MMR maybe required.

In these children the mean interval from exposure to the MMR vaccine to the development of first behavioural symptom was six days, indicating a strong temporal association with exposure to the vaccine. Measles virus nucleocapsid protein antigen has been identified with the follicular dendritic cells in areas of lymphoid nodular hyperplasia in the affected intestine, further implicating a causal role for measles virus in this disease. These children exhibit immunodeficiencies associated with reduced numbers of circulating T lymphocytes. Specific boosting of antiviral immunity in these children could, therefore, be expected to be of therapeutic benefit.

Adoptive transfer of non-antigen-specific cell mediated immunity in humans was first demonstrated by Lawrence in Proc.Soc.Biol.Med 1949; 71; 516. This opened a new avenue of research that has led to an increased understanding of the basic immune mechanisms and to the development of many forms of immunomodulant therapy. Lawrence originally showed that transfer of intact, viable, lymphocytes from a normal tuberculin skin test-positive donor to a skin test-negative recipient, resulted in conversion ("transfer") of the recipient to skin test-positivity.

Lawrence further demonstrated that delayed cutaneous hypersensitivity (DH) responsiveness could be transferred by a soluble, dialysed leucocyte extract (DLE). He termed the factor responsible for this phenomenon "transfer factor" (TF). (TF) could transfer (DH) of a given specificity from a normal skin test-positive donor to a skin test-negative recipient. Moreover, within 6 months, leucocytes from the primary recipient could transfer specific (DH) to a previously skin test-negative secondary recipient.

In addition to transferring non-antigen-specific skin test positivity, DLE preparations containing TF can also initiate other non-antigen-specific cell mediated immune reactions including induction of cytokines such as macrophage migration inhibitory factor (MIF) and leucocyte migration inhibitory factor (LIF). The ability of TF to stimulate LIF production forms the basis for assessing, in vitro, the potency of non-antigen-specific TF.

Despite Lawrence's work the considerable potential for TF as a therapeutic agent capable of transferring specific immunity to individuals who lacked such immunity was not recognised until about 1990. It has recently been used therefore in treatments for chickenpox, herpes virus infections, liver disease and in the treatment of HIV.

Generally human, mouse and bovine TF are small molecules of approximately 3500 to 6000 Daltons. TF is heat labile but cold stable; biological activity remains unimpaired after several years of storage at −20° C. to −70° C. Most studies of the effects of enzymes on the antigen-specific biological activity of TF indicate that it is composed of RNA bases attached to small peptides of at least 8 amino acids. If as seems likely each TF is antigen specific then individual TF's may differ structurally in a manner similar to the subtle variations in antigen-binding sites at the hypervariable region of immunoglobulins or in the T cell receptor for antigens. This specificity is supported by the fact that TF specific for, for example, PPD antigen binds only PPD and no other antigen.

The mechanisms whereby TF participate in the cell-mediated immune response are simply not known. One hypothesis is that TF forms part of the T-lymphocyte receptor (TCR) for antigen and that its presence may be necessary for T cell activation. However, further supportive data are required that are compatible first with the activity of TF in the normal T cell mediated immune response and secondly with the ability of TF to transfer such immunity to a previously non-responsive recipient in an antigen-specific fashion.

In an antigen-responsive subject a small number of T cells bearing receptors for a given antigen are continually present. These membrane receptor sites probably include the TF moiety. Specific antigen binding to the appropriate receptor probably initiates production and the release of more TF which then binds to immunologically uncommitted T lymphocytes rendering them antigen-sensitive and responsive.

Similarly, in transfer of immunity to the non-responsive host, exogenous TF most probably binds to immunologically "virgin" cells. This binding may induce T cell receptor expression with the resulting complex of antigen-specific TF and the T cell receptor forming the specific antigen receptor on the T cell. However, induction of de novo synthesis of the T cell receptor or exposure of the relevant receptor to allosteric effects of transfer factor on membranes proteins should not be excluded.

Although little is known of the mechanism of the action of DLE-TF in vivo more is known of its effects in vitro. In vivo however DLE enhances graft rejection and augments lectin-dependant antibody dependent cellular cytotoxicity. This wide variety of effects of crude DLE reflects the activities of its many different moieties including non-specific adjuvant or inhibitory functions. Antigen-specific properties due to the TF moiety within the DLE include the ability to confer upon non-responsive lymphocytes the ability to react with the relevant antigen in vivo to produce lymphokines in vitro and to enhance antigen-specific T cells cytoxicity against tumour antigens by previously non-responsive cytotoxic cells.

DLE-TF is usually administered by subcutaneous or intramuscular injection, although oral administration appears equally effective. It can also be given intravenously or by suppository or by incorporation into liposomes to prolong its biological activity. Nothing is known about its pharmakinetics.

Further DLE-TF is remarkably free from adverse side effects. Given intramuscularly or subcutaneously an injection may cause pain at the injection site for 10 to 20 minutes and low-grade transient pyrexia may occur but no other significant problems have occurred. However severe pain can be induced at the site of primary or metastatic lesions caused by tumour necrosis when used in cancer therapy.

According therefore to the present invention there is provided a pharmaceutical composition for the treatment of an antigen specific MMR virus mediated disease comprising a soluble dialysed leucocyte extract comprising an antigen specific transfer factor (TF) disposed in a pharmaceutically acceptable carrier or diluent therefor, characterised in that the TF is antigen specific and is formed by the dialysis of virus-specific lymphocytes to a molecular cut-off of 12,500. The TF factor is particularly significant when directed to the measles virus alone but a TF factor for MMR, which is taken to include live attenuated measles vaccine virus, measles virus; mumps vaccine virus and rubella vaccine virus, and wild strains of the aforementioned viruses, or for the other components of MMR (mumps and rubella) is also useful especially for RBD.

The compositions may be particularly adapted for use as a vaccine/immunisation or for use as therapy for IBD or RBD. Preferably the transfer factor is a molecule of approximately 3,500 to 6000 Daltons which is cold stable. The compositions may be adapted for subcutaneous, intra muscular or intravenous injection or for administration by the oral route, by suppository or by incorporation into administrable liposomes.

The invention will now be described, by way of illustration only, with reference to the following examples and the accompanying figures.

FIG. 1 is a comparison of the gene sequence of the majority consequences sequence (MCS*) of the measles virus H region using all wild-type and vaccine strain sequences from GenEMBL on Jun. 1, 1994 with the gene sequence of the vaccine, sporadic wild strains, measles virus H regions isolated from patients with Crohn's disease, ulcerative colitis, autism, inflammatory bowel disease with SSPE strains. The complete sequence between base 8393 and 8550 was determined for each of the genes but only the mutations in them are shown in FIG. 1.

FIG. 2 is a comparison of the gene sequence of the measles virus used in the Japanese measles vaccine with the gene sequence of wild strains and measles F region isolated from a patient with Crohn's Disease.

EXAMPLE 1

Preparation of DLE

Measles virus-specific TF is made from lymphocytes of BALB/c mice immunised by live or killed virus or an antigen derived from such a measles virus. Isolated cells are freeze-thawed and, following micropore filtration the filtrate is added to an immunologically virgin human lumphoblastoid cell line. One cell is serially expanded 10-fold with killed measles virus and interleukin-2, to a billion cells. Measles virus-specific TF preparations are made from this expanded cell population. Cell lysis, dialysis using a 12,500 molecular weight cut-off and a series of concentration procedures results in a TF preparation containing TF and lysozyme. The molecular weight of each preparation used is between 1,800 and 12,000. Appropriate biological markers eg. lysozyme (MW 11,000), horse myoglobin (MW 17.7 KD) and human antibody light chains (MW 22 KD) are used as controls to ensure both the recovery of TF and absence of materials greater than 12,000 MW in the final preparation (viruses are hundreds of millions in molecular weight, and reverse transcriptase of retroviruses is 59 KD). The TF preparation is standardised for potency (vide infra). The ability of TF to stimulate further TF production, and the cross-species reactivity of TF are subsequently exploited in order to produce large amounts of concentrated TF at low cost. This is achieved by injecting the TF preparation into pregnant goats 3 times prior to delivery. Colostrums are collected during the first 3 days post-delivery and TF preparations were made from these by micropore filtration excluding molecules >12,500 mol wt. Following freeze thawing and lyophilising×3 the preparation is tested for potency as described below and standardised at 200 South Carolina units/ml.

EXAMPLE 2

In vitro Determination of Potency

LIF production in response to the defined specific antigen, is measured by the direct assay for inhibition of random leucocyte migration in agarose. Briefly, Leucocytes are incubated with medium 199 only (control) or with medium plus test antigen at 37° C. During this incubation period the neutrophils randomly migrate out of the application weeks to form a circular zone of cells. Responsiveness to antigen is expressed as a migration index (MI). If lymphocytes respond normally to the antigenic challenge, LIF is liberated and prevents or reduces the normal neutrophil random migration. The test is used extensively in the diagnosis of antigen specific cell mediated immune defects. The addition of DLE to this system has two potential effects: firstly, an antigen-independent inhibition of migration at low concentrations of extract, and secondly, antigen-specific induction or enhancements of LIF production at lower concentrations of extract.

DLE-TF potency is determined by taking aliquots of target cells (peripheral blood leucocytes) from 3 normal donors, previously shown to be unresponsive to the test antigen by LMI. Cells are incubated with either 1) medium alone, 2) medium plus antigen, 3) DKE (at 10 serial dilutions) in medium 4, and 4) DLE (in the same 10 serial dilutions) plus antigen plus medium for 30 minutes at 37° C. in a humidified incubator. After 18 hours, migration indices are determined as follows: $MI_A$-antigen dependent LMI produced by non-TF components; and $MI_B$-antigen dependent LMI induced by LIF released from T lymphocytes newly sensitised by TF in the presence of specific antigen. An MIB value <0.90 indicates meaningful antigen-dependent LMI. All concentrations (150 ul) are tested in 6 replicate cultures. If 40 ul provide an MIB of 0.90, then 1 ml of this DLE contains 25 S.C. potency units.

Dose Regimen

One to up to ten, but preferably three or four capsules (20 S.C. units per capsule) per day should be ingested.

Laboratory Monitoring of Clinical Response

It is important to note that there is a marked inter-individual response to any particular batch of DLE-TF.

Patients are monitored immunologically by:

- the ability of DLE-TF MV to restore cutaneous hypersensitivity as measured by the Merieux skin test.
- levels of circulating CD8+CD38+DR+cytotoxic T cells, measured by flow cytometery.
- lymphocyte migration inhibition, as described above.

Another valuable immunological test is antigen-specific T cell cytotoxicity. The use of this test for determination of measles virus-specific cytotoxicity has been described by Fooks et al in virology 1995, 210, 456 to 465. Purified T-lymphocytes are cultured with measles virus infected Raji (B cell) cell line labelled with radiolabelled chromium uninfected cells are used as controls. The specific cytotoxicity of the lymphocytes results in lysis of the infected cells and release of radioisotope from cells of other tumour types. Addition of DLE-TF derived from a donor proven by this test to be responsive to the relevant antigen, enhances the specific cytotoxicity of the patient's lymphocytes in a dose-dependent manner.

The results of Examples 1 and 2 show anecdotally that TF is an effective agent for the treatment of IBD and as a vaccine for measles virus.

EXAMPLE 3

In order to investigate a consecutive series of children for a new syndrome comprising chronic enterocolitis and regressive behavioural disorder (RBD) 12 children with a mean age of 6 years, range 3 to 10, all but one of whom were male, were referred with a history of achievement of normal developmental milestones followed by loss of acquired skills including language along with bowel symptoms, diarrhoea, abdominal pain and in some cases food intolerance all associated with the presence of MMR viruses in the gut.

The children underwent gastroenterolgical, neurological and developmental assessment including review of prospective in developmental records. Under sedation, ileo-colonoscopy and biopsy, MRI, EEG, and lumbar puncture were performed. Barium follow-through was undertaken where possible. Chemistry, haematology and immunology profiles were examined.

It was found that the onset of behavioural symptoms were associated with MMR (mumps, measles and rubella vaccinations) in 8 of the 12 children and with measles infections one child otitis media in another. All 12 children had significant intestinal pathology ranging from lymphoid nodular hyperplasia to aphthoid ulceration. Histology revealed patch chronic inflammation in the colon in 11 cases and reactive ileal lymphoid hyperplasia in 7 cases, but no granulomas. One case had ileal lymphoid nodular hyperplasia alone diagnosed on barium follow-through. Behaviourally, they all formed a heterogeneous diagnostic group which included autism (9/12), disinteragrative psychosis (1/12) and possible post-viral/vaccinial encephalitis (2/12). All the children exhibited features of severe developmental regression. Clinically they had no focal neurological abnormalities and MRI and EEG studies were within normal limited. Table 1 and 2 summarise the above endoscopic, histological and neuropsychiatric diagnosis.

Accordingly a significant gastrointestinal pathology has been identified in association with behavioural regression in a selected group of previously, apparently normal children. In the majority there is therefore a clear association with possible environmental triggers.

EXAMPLE 4

The persistence of measles virus infection and the immunological status of children with a combination of regressive developmental disorder, ileo-colonic lymphoid nodular hyperplasia and non-specific colitis was investigated.

Detection of Viral Antigen

Vero (African green monkey kidney) cells were cultured and infected with HU-2 strain measles. After two days, when the characteristic syncytial cytopathic effect was observed, the cell layers were washed with PBS and harvested using a cell scraper. The cells were disrupted using a sonicator, in 1 ml lysis buffer (8M urea, 150 mM β-mercaptoethanol, 50 mM Tris-HCl pH 7.5) on ice, at a concentration of $10^7$ cells/ml. Undisrupted cells and cell debris were removed by centrifugation (1500×g, 20 min, 4° C.). Uninfected Vero cells were cultured and lysed in an identical manner to the infected cells and used as controls. 4 μl of each cell lysate was fractionated by SDS-PAGE and transferred to a nitrocellulose membrane in a tank transfer system at 200 mA for 16 h. 1.4 μg of purified measles virus nucleocapsid protein expressed in Sf9 cells served as a positive control. Transfer of equal amounts of protein was confirmed by Ponceau staining. Following saturation in blocking buffer (phosphate buffered saline [PBS], 0.1% v/v Tween-20 containing 5% w/v skimmed milk powder) for 1 h at room temperature, the filters were incubated with either $RAd68^+$ or preimmune serum at a 1:5 000 dilution of blocking buffer. After three washes in PBST (PBS, 0.1% v/v Tween-20) each for 10 min, the membranes were incubated in a 1:1 000 dilution of second antibody (horseradish peroxidase-conjugated anti-mouse immunoglobulins) in PBST for 1 h at room temperature. Following a further three washes in PBST each for 10 min, the immunoassay was developed using the ECL detection system according to the manufacturer's instructions. Western blot analysis was also performed, in an identical manner, on protein extracted from normal human intestinal tissue.

The strong immunoreactivity of $RAd68^+$ with the measles N-protein was observed. No signal was obtained using either the corresponding preimmune serum or following application of $RAd68^+$ to the protein extract from uninfected cells. Western blot analysis $RAd68^+$ on extracted normal human intestine gave no signal. This confirms the specificity of the measles virus antisera to be used on affected intestinal tissues.

Immunocytochemistry

The specificity of $RAd68^+$ for measles virus was examined further by immunocytochemistry using mumps virus—a related paramyxovirus—and rubella virus as controls. Measles virus (HU-2 strain), mumps virus (Urabe strain), and rubella virus infected Vero cells were prepared separately and processed for immunocytochemistry using an immunoperoxidase technique as described previously. Uninfected Vero cells were used as negative controls of $RAd68^+$ and the primary mumps and rubella virus antibodies.

Since the $RAd68^+$ had been raised in an adenovirus type-5 construct, the likelihood of cross-reactivity with adenovirus antigens was examined. When $RAd68^+$ was applied to either adenovirus-infected intestinal tissue or a commercial preparation of HeLa cells infected with adenovirus-type 5 it produced specific staining in both. In view of this cross-reactivity, parallel sections from the biopsy series of 12 children were immunostained for both measles virus N-protein and adenovirus, the latter using a commercial adenovirus antibody that identified the relevant type-5 strain, in order to discriminate the presence of these different virus antigens within tissues. In addition, murine antiserum raised in an identical manner to $RAd68^+$ but without the measles virus N-gene ($RAd68^-$), was applied to both measles and adenovirus infected cells and tissues. Negative controls also included sections incubated with normal mouse serum at a dilution of 1:300, based upon measurement of the total serum protein concentration and calculation of the estimated IgG fraction. Sections which were developed following omission of the primary measles virus antiserum served as a further control.

When $RAd68^+$ was applied to sections of measles virus infected and uninfected Vero cells positive cytoplasmic staining was observed in infected cells only in areas of characteristic syncytial cytopathic effect. No staining was seen when either $RAd68^+$ was omitted, when sections were incubated with the pre-immune mouse serum or when $RAd68^-$ genes were added in place of $RAd68^+$.

In both mumps and rubella virus infected cells, positive cytoplasmic staining was observed following addition of the specific primary antibody. Conversely, no staining was observed with either $RAd68^+$ or following omission of the respective primary antibodies. $RAd68^+$ and $RAd68^-$ applied to HeLa cells infected with adenovirus type-5 produced positive nuclear staining, consistent with the origin of the vector used to raise the antisera.

Adsorption of $RAd68^+$ $Rad68^+$ was applied in triplicate to wells of 96 well plates prepared commercially for ELISA using lysed measles virus infected cells as the antigen. The wells were incubated for 1 hour then the supernatants were transferred to new wells. This procedure was repeated 5 times. The resulting supernatants were applied to measles virus infected cells and tissues (brain—SSPE(subacute sclerosing panencephalitis), gut) and developed as described above. $RAd68^+$, processed similarly on control wells containing uninfected cells lysates, were applied to serial tissue sections for comparison.

Following absorption of $RAd68^+$ on whole measles antigen, the signal was greatly reduced in measles virus infected tissue, both in terms of numbers of positively stained cells and staining intensity, compared with $RAd68^+$ adsorbed in control wells containing uninfected cells. The latter produced a strongly positive signal in measles virus infected tissue which was identical to the unadsorbed antiserum.

Tissue Studies

Intestinal biopsies from the 12 children were taken. This included single terminal ileal biopsies from 9 children and a total of 52 colonic biopsies including samples from rectum through to caecum from all 12 children. Serial sections from each biopsy were stained immunohistochemically for the following viruses: measles, rubella, Herpes simplex, mumps, adenovirus and human immunodeficiency virus (HIV). Control tissues included sections developed either following omission of the primary antibody, or with the corresponding pre-immune serum or immunoglobulin fraction.

Positive controls for measles virus infection included post-mortem tissues from one case of SSPE, one case of measles inclusion body encephalitis (MIBE), and tissue from an acutely infected small intestine of in an African child with AIDS who was suffering from measles pneumonia.

Control intestinal biopsy samples were obtained from 10 children in whom the initial colonoscopic findings were reported as normal. A total of 70 sections were studied, including those from ileum, caecum, colon and rectum.

In addition, 10 archival age-matched terminal ileal biopsies were studied from children with Crohn's disease, selected consecutively on the basis that the haematoxylin and eosin stained section contained at least one lymphoid follicle with its associated germinal centre.

Lymph node biopsy specimens from 6 patients with lymphadenopathy and AIDS were also immunostained with $RAd68^+$ and primary HIV antibody.

The ileal biopsy sections from 5 children were examined by double immunohistochemical labelling for measles virus-N protein and follicular dendritic cells using CD21 monoclonal antibody. The sections were incubated with normal goat serum for 20 min followed by application of measles virus primary antibody ($RAd68^+$) overnight at 4° C. Sections were washed three times for 5 minutes in Tris-buffered saline (TBS). Thereafter biotinylated goat-anti rabbit antibody was applied at 1:200 dilution plus normal human serum for 30 min at room temperature. A blocking murine monoclonal anti-Pneumocystis carinii antibody was then applied at a dilution of 1:20 for 60 min, followed by goat-anti mouse Fab fraction at 1:20 dilution for 30 min at room temperature. The initial development step consisted of streptavidin ABC at a 1:1:200 dilution for 30 min at room temperature followed by addition of diaminobenzidine. Sections were then microwaved for 20 min in citrate buffer at pH 6.0 followed by application of monoclonal CD 21 at a dilution of 1:20 for 60 min at room temperature. After washing three times in TBS, alkaline phosphatase conjugated sheep anti-mouse monoclonal antibody was added for 75 min at room temperature, and the sections were finally developed with Fast Red. Controls included omission of either primary antibody, both primary antibodies, or incubation with the blocking murine monoclonal anti-P. carinii antibody alone.

MIBE and SSPE serve-as a useful comparison for examining measles virus antibody specificity. Both represent brain tissue that is persistently infected with measles virus, although the pattern of staining is characteristic in the two conditions. In sections of MIBE, $RAd68^+$ produced positive staining in cells containing distinctive, large nuclear inclusion bodies. In SSPE, staining for measles virus was detected in inflammatory foci, specifically in neurones, microglia and endothelial cells that did not exhibit the characteristic cytopathic change of MIBE.

Hence, $RAd68^+$ distinguished the pattern of measles virus immunostaining between the two diseases, and no staining was seen on brain sections either from which the primary antibody had been omitted or $RAd68^-$ substituted for $RAd68^+$.

In acute measles virus infection of the small intestine, staining was detected in discrete foci of epithelial cells in 2 of 4 Peyer's patches, and in occasional lymphocytes and endothelial-like cells within the lamina propria and submucosa.

In both the measles virus and adenovirus infected intestinal tissues, infected cells exhibited cytopathic vacuolation that was not seen in adjacent cells which presumably, were not infected.

In the 9 terminal ileal biopsies from children with intestinal pathology and associated behaviour disorder, 7 contained a complete lymphoid follicle with its associated germinal centre. In 2 cases, where these structures had been previously identified in haematoxylin and eosin-stained sections, resulting in them having been cut out due to multiple sampling.

Positive measles virus immunostaining was identified using $RAd68^+$ in 5 of the 7 cases. Positive staining was confined exclusively to the germinal centres of lymphoid follicles. Staining was punctate, and its distribution appeared to follow the cytoplasm or cytoplasmic membrane of cells with an extensive cytoplasm. An identical pattern of staining was observed in HIV infected lymphocytes stained with HIV primary antibodies.

Positive staining for measles was detected in children for whom the onset of symptoms had been associated with a clinical episode of measles in 1 case (but previously vaccinated with MMR) and MMR in 3 cases. In the case of the fifth positive child, no exposure had been noted: onset of behavioural symptoms started at 18 months and his only recorded exposure to either measles or rubella had been as MMR at 16 months of age.

Double immunostaining of ileal biopsies with $RAd68^+$ and CD21 confirmed that the measles virus signal localised to follicular dendritic cells. A similar pattern of staining was seen in the specimen of small intestine that was acutely infected with the measles virus.

Out of a total of 52 colonic biopsies, 5 individual biopsies from different children showed lymphoid follicles, all of which exhibited reactive hyperplasia. None of these 52 biopsies were positive for measles virus.

Of the 10 control colonoscopic biopsy series, blinded histological examination confirmed normal appearances in 5 of these cases. Of the remaining 5 cases, small focal collections of subepithelial chronic inflammatory cells were found in one case, one case showed mild focal neutrophil infiltration of the lamina propria, while the 3 remaining cases, one of which turned out to be from a child with ulcerative colitis in remission, had reactive follicular hyperplasia of the terminal ileum. Only one control biopsy stained positively for measles virus; that of the child with the ulcerative colitis, in whom a germinal centre in a focus of ileal lymphoid nodular hyperplasia stained in an identical pattern to that above.

Of the 10 terminal ileal biopsies from children with Crohn's disease, 9 contained a complete lymphoid follicle with its associated germinal centre. Two cases exhibited severe inflammation while the remainder showed only mild inflammation, with an increase in lamina propria mononuclear cells but no ulceration. No granulomas were identified in these sections. None of the germinal centres were positive from measles virus. In only one case was a positive signal obtained—in a single endothelial cell.

None of the tissues from either the affected children or the positive or negative controls showed evidence of immunostaining for mumps, adenovirus or Herpes simplex virus. Only those lymph nodes from HIV-positive individual with AIDS exhibited positive immunostaining with the HIV primary antibody: characteristically, this was confined to follicular dendritic cells. Rubella antibody produced focal positive staining in brain tissue from a case of congenital rubella syndrome and some non-specific staining was seen occasionally in the laminar propria of both normal and diseased intestine.

Each antibody gave a signal that was appropriate for its respective target antigen in infected positive control cells and/or tissue. No signal was seen in sections treated with either corresponding normal serum or without respective primary antibody.

Detections of Viral RNA

The RNA from the peripheral blood mononuclear cells (PBMC) of fourteen children with RBD was analysed for the presence of both measles virus H and N gene RNAs. Negative controls were used consisting of RNA from both uninfected human umbilical vein endothelial cells (HUVEC) and a rat hepatoma cell line.

In the affected children 5 ml of blood was taken in EDTA tubes and PBMC was isolated on ficoll density gradient. Cells were wash in PBS, pelleted, and stored at −70° C. until RNA extraction.

Total RNA was extracted from coded PBMC samples using an acid guanidinium phenol-chloroform method. The RNA pellets were washed twice with 70% ethanol, resuspended in 30 $\mu$l of water and stored at −70° C. Thereafter 100 ng of total RNA from PBMC was used in a combined RT-PCR reaction using rTth DNA polymerase and EZ buffer with primers U1A1 and U1A2 according to the manufacturer's instructions. Forty thermal cycles were performed using the following cycling parameters. Reaction mixtures were incubated at 68° C. for 30 min followed by a denaturation step of 95° C. for 3 min. Reactions were then subjected to a further forty thermal cycles of 95° C. for 1 min and 58° C. for 1 min. After a final extension at 60° C. for 7 min, the reaction mixtures were cooled and 10 $\mu$l of PCR product electrophoresed on a 1.2% agarose gel. PCR products were visualised under ultra violet light and transferred to our Hybond-N membrane. Southern hybridization was also performed on the membrane using a $^{32}$P-labelled internal oligonucleotide probe (U1A). Positive bands were extracted from agarose gel using butanol. Direct sequencing of amplification products was carried out using a Taq Dye Primer sequencing kit and analysed using a 373AA DNA sequencer.

Measles virus H gene, but no N-gene cDNA was amplified from duplicate PBMC-RNA samples from 6 of the 14 affected children (sequence data from 3 of these children plus one case of Crohn's disease and one case of ulcerative colitis and controls are shown in FIG. 1), One children whose biopsy was positive for the N-gene using PCR also stained positive for the measles virus N-protein antigen. Sequence analysis of the amplification product showed it to be consistent with Schwarz vaccine-strain measles virus. Measles H and N gene cDNAs were also amplified from measles virus infected HUVEC but not from either PBMC-derived RNA from the 6 cases of SSPE or any of the negative controls. Sequence data from RNA derived from 6 brain tissues affected by SSPE are included in FIG. 1.

Detection of Viral Antibodies

Serum samples from 22 children affected with ileo-colonic lymphoid nodular hyperplasia, regressive development disorder and non-specific colitis were compared with 32 control children. The control group consisted of 13 normal children and 19 paediatric patients admitted for routine surgery. Males predominated in the control group and all children were under 10 years of age. For all but one of the affected children and all controls, none had been re-vaccinated against measles.

CSF samples were available from 6 of the children with the syndrome. Serum and CSF IgG and IgM antibody immunoreactivity to measles, rubella, mumps viruses and cytomegalovirus (CMV) was examined by ELISA according to the manufacturer's instructions. For IgM assays, all samples were pre-treated to absorb IgG and Rheumatoid Factor. In order to exclude a non-specific polyclonal elevation in either IgG or IgM, total serum IgG and IgM levels were measured in affected children. All samples were analysed in duplicate, in parallel with standard positive and negative control sera.

The mean measles virus IgG immunoreactivity, as detailed in Table 1, was 4090 (SEM±846) MIU/ml for affected children and 2005(SEM±329) MIU/ml for the controls. The difference between the means is statistically significant (p=0.02). The difference in mean values for rubella virus IgG immunoreactivity was not statistically significant when affected children (59{SEM±18}IU/ml) and controls (462{SEM±9}IU/ml) were compared (p>0.4). Neither serum measles nor rubella IgM immunoreactivities were elevated. Measles and rubella IgG and IgM antibodies were undetectable in CSF samples from affected children.

The IgG immunoreactivity for mumps virus and cytomegalovirus were also ascertain in the affected and control children. The results are detailed in Table 1.

In order to exclude a non-specific IgG response, the relationship between measles virus specific IgG immunoreactivity and total IgG concentration was examined in affected children. Using logistic regression, no statistically significant relationship was observed (p>0.7). In addition, there was no statistically significant relationship between measles IgG and rubella IgG immunoreactivities in affected children (p>0.4).

TABLE 1

| | Serology (Mean ± SEM) | | | |
|---|---|---|---|---|
| | Measles | Mumps | Rubella | CMV |
| Affected cases | 4090(±846) | 699(±169) | 59(±18) | 3 positive |
| Control cases | 2005(±329) | 723(±156) | 46 (±9) | 7 positive |

Immunocytological Profiles

Peripheral blood samples from a total of 12 affected children were analysed for total lymphocyte count (CD3), helper T cells (CD4), cytotoxic/suppressor T cells (CD8), B cells (CD19), and natural killer cells (CD16). CD4:CD8 ratios were also analysed. In the 12 children all but one showed some degree of immunodeficiency, as defined by low numbers of circulating immune cells. All data are age-adjusted.

TABLE 2

| Type of cells | No. of children with low values | Mean value of lower limit ($\times 10^6$ cells/ml) | Range of low values ($\times 10^6$ cells/ml) | Normal value at 3 yrs ($\times 10^6$ cells/ml) | Normal value at 9 yrs ($\times 10^6$ cells/ml) |
|---|---|---|---|---|---|
| T cells | 10 | 0.54 | 0.3–1.12 | 2.33–4.10 | 0.84–3.74 |
| CD4 | 8 | 0.27 | 0.06–0.6 | 1.27–3.02 | 0.54–2.50 |
| CD8 | 10 | 0.22 | 0.05–0.34 | 0.81–1.54 | 0.34–1.84 |
| B cells | 10 | 0.24 | 0.02–0.46 | 0.5–1.5 | 0.2–1.6 |
| NK | 10 | 0.11 | 0.01–0.21 | 0.3–0.7 | 0.08–0.90 |

The above tabulated data suggests that children with colitis and regressive developmental disorder have an acquired immunodeficiency in addition to persistent measles virus infection of ileal lymphoid tissue.

The pattern of measles virus immunostaining was quite distinct from that observed previously in Crohn's disease, where it was restricted to macrophages and endothelial cells in foci of granulomatous inflammation. The absence of staining is the ileal lymphoid follicles in both Crohn's disease and other control tissues indicates that in the present case of lymphoid nodular hyperplasia, the reaction is not only specific, but may also represent a novel pathogenic mechanism for measles virus. An influence from both the above clinical and virological data appears to be that either the vaccine strain of the measles virus, or its associated antigens, are capable of persisting within intestinal tissue.

EXAMPLE 5

The gene sequences of vaccine and wild-type measles virus H region were determined using known methods and the majority consequences sequence of the measles virus H region sequences using all wild-type and vaccine strain sequences for GenEMBL on Jun. 1, 1994 was also determined, as shown in FIG. 1. These sequences were then compared to the gene sequence of the H region of measles virus isolated from patients with Crohn's disease, ulcerative colitis and autism, as shown in FIG. 1. As the sequences show two of the patients, one with ulcerative colitis and the other with autism had the same single amino acid mutation at base 8419 as the vaccine (Schwarz). None of the patients had exactly the same gene sequence as the majority consequences sequence or any of the sporadic wild strains. As shown in FIG. 1 the same sequence of the H region was also compared with the gene sequence of measles isolated from IBD patients with SSPE strains.

The sequence of the F region of a Japanese strain AIK-C used in the MMR vaccine, along with the sequence of the F region of various wild strains were compared with the gene sequence of the F region of a measles virus isolated from a patient with Crohn's disease. As can be seen from FIG. 2, the F region of the measles virus isolated from the patient with Crohn's disease has the same single amino acid mutation at base 5384, 5397, 5409 and 5449 as variants of the sporadic wild strains. The mutation at 5449 alters an ATG codon. The ATG sequence being known as a STOP/START codon.

Accordingly, the F region of the measles gene is thought to be important in patients with Crohn's disease.

Key for Table 3

LNH=Lymphoid nodular hyperplasia

Normal Range Units

Haemoglobin(Hb) 11.5–14.5 g/dl

Packed cell volume (PCV) 0.37–0.45

Mean cell volume (MCV) 76–100 pg/dl

Platelets 140–400 $10^9$/l

White cell count (WBC) 5.0–15.5 $10^9$/l

Lymphocytes 2.2–8.6 $10^9$/l

Eosinophils 0–0.4 $10^9$/l

ESR 0–15 mm/hr

IgG 8–18 g/l $IgG_1$ 3.53–7.25 g/l $IgG_4$ 0.1–0.99 g/l

IgA 0.5–0.28 g/l

IgM 0.6–2.8 g/l

IgE 0–62 g/l

What is claimed is:

1. A method for the diagnosis of Regressive Behavioral Disease from a body derived sample which method comprises contacting a body derived sample with reagents to perform an assay for detection of persistent measles virus infection in said sample, detecting the presence or absence of persistent measles virus infection in the sample wherein the presence of persistent measles virus infection is indicative of Regressive Behavioral Disease.

2. The method of claim 1 wherein the assay is performed for detection of persistent wild or vaccine mediated measles virus in affected material.

3. The method of claim 1 wherein the assay comprises detection of a viral antigen, viral RNA or viral antibodies.

* * * * *

```
                         SEQUENCE LISTING

<160> NUMBER OF SEQ ID NOS: 11

<210> SEQ ID NO 1
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 1

tgcttccagc                                                    10


<210> SEQ ID NO 2
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 2

caagcactct                                                    10


<210> SEQ ID NO 3
<211> LENGTH: 20
<212> TYPE: DNA
<213> ORGANISM: Artificial Sequence
<220> FEATURE:
<223> OTHER INFORMATION: Majority consequences sequence.

<400> SEQUENCE: 3

ccattgaagg ataacaggat                                         20


<210> SEQ ID NO 4
```

-continued

<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 4
gtgtattggc 10

<210> SEQ ID NO 5
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 5
gccaatgaag 10

<210> SEQ ID NO 6
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 6
taggtgtaat 10

<210> SEQ ID NO 7
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 7
tccttcatac 10

<210> SEQ ID NO 8
<211> LENGTH: 50
<212> TYPE: DNA
<213> ORGANISM: Artificial Sequence
<220> FEATURE:
<223> OTHER INFORMATION: Majority consequences sequence.

<400> SEQUENCE: 8
ctgttgatct gagtctgaca gttgagctta aaatcaaaat tgcttcggga 50

<210> SEQ ID NO 9
<211> LENGTH: 141
<212> TYPE: DNA
<213> ORGANISM: Measles virus

<400> SEQUENCE: 9
ctccaagtcc cccggtctcc tcctcttctc gaagggacca aaagatcaat ccaccacacc 60
cgacgacact caactcccca cccctaaagg agacaccggg aatcccagaa tcaagactca 120
tccaatgtcc atcatgggtc t 141

<210> SEQ ID NO 10
<211> LENGTH: 10
<212> TYPE: DNA
<213> ORGANISM: Artificial Sequence
<220> FEATURE:
<223> OTHER INFORMATION: Majority consequences sequence.

-continued

```
<400> SEQUENCE: 10

cggttcaggg                                                            10


<210> SEQ ID NO 11
<211> LENGTH: 10
<212> TYPE: DNA
<213> ORGANISM: Artificial Sequence
<220> FEATURE:
<223> OTHER INFORMATION: Majority consequences sequence.

<400> SEQUENCE: 11

acaaatccaa                                                            10
```